US006650934B2

(12) United States Patent
Murdock

(10) Patent No.: US 6,650,934 B2
(45) Date of Patent: *Nov. 18, 2003

(54) POLYMERIC FOAM RESERVOIRS FOR AN ELECTROTRANSPORT DELIVERY DEVICE

(76) Inventor: Thomas O. Murdock, 3999 Clover Ave., Vadnais Heights, MN (US) 55127

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 9 days.

(21) Appl. No.: 08/966,437

(22) Filed: Nov. 7, 1997

(65) Prior Publication Data
US 2002/0042587 A1 Apr. 11, 2002

Related U.S. Application Data
(60) Provisional application No. 60/033,023, filed on Dec. 17, 1996.

(51) Int. Cl.⁷ ................................................. A61N 1/30
(52) U.S. Cl. .................. 604/20; 604/22; 264/494; 424/449; 521/141
(58) Field of Search ............... 604/20–22; 424/449, 424/448; 264/494; 521/141

(56) References Cited

U.S. PATENT DOCUMENTS

| 3,912,665 A | 10/1975 | Spitzer et al. ........... 260/2.5 E |
| 4,164,226 A | 8/1979 | Tapper .................. 128/419 R |
| 4,239,046 A | 12/1980 | Ong ............................. 128/650 |
| 4,330,634 A * | 5/1982 | Rodaway .................... 521/134 |
| 4,524,064 A | 6/1985 | Nambu ......................... 424/81 |
| 4,530,806 A * | 7/1985 | Melchoir |
| 4,642,267 A * | 2/1987 | Creasy et al. ............... 428/413 |
| 4,664,857 A | 5/1987 | Nambu ......................... 264/28 |
| 4,731,926 A | 3/1988 | Sibalis .......................... 29/877 |
| 4,734,097 A | 3/1988 | Tanabe et al. ................. 623/11 |
| 4,752,285 A | 6/1988 | Petelenz et al. ............... 604/20 |
| 4,786,277 A | 11/1988 | Powers et al. ................. 604/20 |
| 4,808,353 A | 2/1989 | Nambu et al. ................. 264/28 |
| 4,856,188 A | 8/1989 | Sibalis .......................... 29/877 |
| 4,883,457 A | 11/1989 | Sibalis ......................... 604/20 |
| 4,925,603 A | 5/1990 | Nambu ......................... 264/28 |
| 4,988,771 A | 1/1991 | Takeuchi et al. ............. 525/276 |
| 4,989,607 A | 2/1991 | Keusch et al. ............... 128/640 |
| 5,002,527 A | 3/1991 | Reller et al. .................. 604/20 |
| 5,053,001 A | 10/1991 | Reller et al. .................. 604/20 |
| 5,080,646 A | 1/1992 | Theeuwes et al. ............ 604/20 |
| 5,141,973 A | 8/1992 | Kobayashi et al. ......... 523/300 |

(List continued on next page.)

FOREIGN PATENT DOCUMENTS

| DE | 410009 | 5/1934 | |
| EP | 0 516 026 A1 | 12/1992 | .......... A61K/47/32 |
| EP | 0 623 345 A1 | 11/1994 | .......... A61K/31/485 |
| WO | WO 81/00785 | 3/1981 | |

OTHER PUBLICATIONS

Kirk–Othmer, 4th Ed., vol. 11, Wiley & Sons (1994), pp 730–763, "Foamed Plastics".

(List continued on next page.)

Primary Examiner—Brian L. Casler
Assistant Examiner—Jeremy Thissell

(57) ABSTRACT

A method is provided for preparing a novel therapeutic agent-containing reservoir (26, 28) for use in conjunction with an electrotransport drug delivery system (10). A polymeric matrix is foamed in a selected atmosphere and then cross-linked to form a polymeric closed-cell foam matrix reservoir (26, 28). The method enables relatively smaller quantities of therapeutic agent to be loaded into the electrotransport system (10) and is especially useful for the transdermal delivery of more costly drugs, such as peptides and proteins produced from genetically engineered cell lines, and/or highly potent drugs for which a small dosage is efficacious. Reservoirs (26, 28) prepared according to this method and electrotransport devices (10) containing such reservoirs are also provided.

19 Claims, 1 Drawing Sheet

U.S. PATENT DOCUMENTS

| | | | | |
|---|---|---|---|---|
| 5,143,071 | A | 9/1992 | Keusch et al. | 128/640 |
| 5,147,296 | A | 9/1992 | Theeuwes et al. | 604/20 |
| 5,167,617 | A | 12/1992 | Sibalis | 604/20 |
| 5,169,382 | A | 12/1992 | Theeuwes et al. | 604/20 |
| 5,169,383 | A | 12/1992 | Gyory et al. | 604/20 |
| 5,279,543 | A | 1/1994 | Glikfeld et al. | 604/20 |
| 5,302,172 | A | 4/1994 | Sage, Jr. et al. | 604/20 |
| 5,318,514 | A | 6/1994 | Hofmann | 604/20 |
| 5,354,790 | A | 10/1994 | Keusch et al. | 523/300 |
| 5,356,632 | A | 10/1994 | Gross et al. | 424/449 |
| 5,358,483 | A | 10/1994 | Sibalis | 604/20 |
| 5,362,307 | A | 11/1994 | Guy et al. | 604/20 |
| 5,370,115 | A | 12/1994 | Ogawa et al. | 128/639 |
| 5,374,241 | A | 12/1994 | Lloyd et al. | 604/20 |
| 5,697,896 | A * | 12/1997 | McNichols et al. | |
| 6,169,123 | B1 * | 1/2001 | Cercone | 521/134 |

OTHER PUBLICATIONS

Encyclopedia of Polymer Science and Engineering, vol. 7, (1987) "Gels", pp 514–531.

Encyclopedia of Polymer Science and Engineering, vol. 4, "Cross–Linking, Reversible", pp 395–417.

Encyclopedia of polymer Science and Engineering, vol. 4, "Cross–Linking", pp 350–395.

Encyclopedia of Polymer Science and Engineering, vol. 4, "Cross–Linking with Radiation", pp 418–449.

Gehrke, Stevin H. and Lee, Ping I, Specialized Drug Delivery Systems, Chapter 8, pp 333–392.

Encyclopedia of Pharmaceutical Technology, vol. 7, pp 441–465, "Hydrogels".

Encyclopedia of Polymer Science and Engineering, vol. 7, 1987, pp 783–807, "Hydrogels".

* cited by examiner-

POLYMERIC FOAM RESERVOIRS FOR AN ELECTROTRANSPORT DELIVERY DEVICE

CROSS REFERENCE TO RELATED APPLICATIONS

Applicant claims priority under 35 USC 119(e) based upon the earlier filed co-pending provisional application filed on Dec. 17, 1996, Ser. No. 60/033,023, now abandoned.

TECHNICAL FIELD

This invention relates generally to electrotransport drug delivery. More particularly, the invention relates to a novel method of making a new type of drug reservoir for incorporation into an electrotransport drug delivery system. The invention additionally relates to new drug reservoirs, and to electrotransport drug delivery systems containing these reservoirs.

BACKGROUND ART

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

However, many drugs are not suitable for passive transdermal drug delivery because of their size, ionic charge characteristics and hydrophilicity. One method of overcoming this limitation in order to achieve transdermal administration of such drugs is the use of electrical current to actively transport drugs into the body through intact skin. The method of the invention relates to such an administration technique, i.e., to "electrotransport" or "iontophoretic" drug delivery.

Herein the terms "electrotransport", "iontophoresis", and "iontophoretic" are used to refer to the transdermal delivery of pharmaceutically active agents by means of an applied electromotive force to an agent-containing reservoir. The agent may be delivered by electromigration, electroporation, electroosmosis or any combination thereof. Electroosmosis has also been referred to as electrohydrokinesis, electro-convection, and electrically induced osmosis. In general, electroosmosis of a species into a tissue results from the migration of solvent in which the species is contained, as a result of the application of electromotive force to the therapeutic species reservoir, i.e., solvent flow induced by electromigration of other ionic species. During the electrotransport process, certain modifications or alterations of the skin may occur such as the formation of transiently existing pores in the skin, also referred to as "electroporation". Any electrically assisted transport of species enhanced by modifications or alterations to the body surface (e.g., formation of pores in the skin) are also included in the term "electrotransport" as used herein. Thus, as used herein, the terms "electrotransport", "iontophoresis" and "iontophoretic" refer to (1) the delivery of charged drugs or agents by electromigration, (2) the delivery of uncharged drugs or agents by the process of electroosmosis, (3) the delivery of charged or uncharged drugs by electroporation, (4) the delivery of charged drugs or agents by the combined processes of electromigration and electroosmosis, and/or (5) the delivery of a mixture of charged and uncharged drugs or agents by the combined processes of electromigration and electroosmosis.

Systems for delivering ionized drugs through the skin have been known for some time. British Patent Specification No. 410,009 (1934) describes an iontophoretic delivery device which overcame one of the disadvantages of the early devices, namely, the need to immobilize the patient near a source of electric current. The device was made by forming, from the electrodes and the material containing the drug to be delivered, a galvanic cell which itself produced the current necessary for iontophoretic delivery. This device allowed the patient to move around during drug delivery and thus required substantially less interference with the patient's daily activities than previous iontophoretic delivery systems.

In present electrotransport devices, at least two electrodes are used. Both of these electrodes are disposed so as to be in intimate electrical contact with some portion of the skin of the body. One electrode, called the active or donor electrode, is the electrode from which the drug is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device. If the ionic substance to be driven into the body is positively charged, then the positive electrode (the anode) will be the active electrode and the negative electrode (the cathode) will serve as the counter electrode, completing the circuit. If the ionic substance to be delivered is negatively charged, then the cathodic electrode will be the active electrode and the anodic electrode will be the counter electrode.

Existing electrotransport devices additionally require a reservoir or source of the pharmaceutically active agent which is to be delivered or introduced into the body. Such drug reservoirs are connected to the anode or the cathode of the electrotransport device to provide a fixed or renewable source of one or more desired species or agents.

Thus, an electrotransport device or system, with its donor and counter electrodes, may be thought of as an electrochemical cell having two electrodes, each electrode having an associated half cell reaction, between which electrical current flows. Electrical current flowing through the conductive (e.g., metal) portions of the circuit is carried by electrons (electronic conduction), while current flowing through the liquid-containing portions of the device (i.e., the drug reservoir in the donor electrode, the electrolyte reservoir in the counter electrode, and the patient's body) is carried by ions (ionic conduction). Current is transferred from the metal portions to the liquid phase by means of oxidation and reduction charge transfer reactions which typically occur at the interface between the metal portion (e.g., a metal electrode) and the liquid phase (e.g., the drug solution). A detailed description of the electrochemical oxidation and reduction charge transfer reactions of the type involved in electrically assisted drug transport can be found in electrochemistry texts such as J. S. Newman, *Electrochemical Systems* (Prentice Hall, 1973) and A. J. Bard and L. R. Faulkner, *Electrochemical Methods, Fundamentals and Applications* (John Wiley & Sons, 1980).

The present invention is directed to novel polymeric foam matrix drug reservoirs for use in conjunction with an electrotransport drug delivery system and methods of making these new reservoirs. In contrast to methods for making prior drug reservoirs for use in such systems and in contrast to prior drug reservoirs, the present method provides a reservoir that enables smaller quantities of drug to be loaded into the system. This is an important consideration with respect to more costly drugs, such as peptides and proteins produced from genetically engineered cell lines, and/or highly potent drugs for which a small dosage is efficacious. With such drugs, it is desirable to decrease the amount of drug loaded into the reservoir.

Typically, for drug delivery using transdermal drug delivery devices it is preferred that drug flux is independent of the concentration of drug in the reservoirs. Decreasing drug loading has the effect of decreasing the concentration of drug in the reservoir to a point where drug flux becomes dependent on reservoir drug concentration. Thus, it is desirable to maintain higher drug concentration in the drug reservoir.

Although it is possible to reduce both the drug loading and the volume of the reservoir, thereby maintain the drug concentration above a level required for concentration-independent drug flux, there are limits on how small the drug reservoir may be. For example, if the volume of the donor reservoir is reduced by decreasing the skin contact area the potential for skin irritation, i.e., irritation caused by the applied electric current and/or the drug being delivered, increases. If the volume of the donor reservoir is reduced by decreasing the thickness of the reservoir, the potential for electrical shorting between the electrodes and the skin increases. In addition, thinner reservoirs are inherently more difficult to manufacture with precise uniformity.

Thus, there is a need for a method of reducing electrotransport donor reservoir drug loading without reducing reservoir size or volume.

DESCRIPTION OF THE INVENTION

Accordingly, it is a primary aspect of the invention to provide a method for preparing a novel drug reservoir for use in conjunction with an electrotransport drug delivery system, which overcomes the above-mentioned limitations in the art.

It is another aspect of the invention to provide a method for making a novel therapeutic agent-containing polymeric foam reservoir having a predetermined volume for use in electrotransport drug delivery, which method involves foaming a polymeric matrix that contains a cross-linkable polymer.

It is still another aspect of the invention to provide such a method which involves foaming an admixture of a therapeutic agent and a polymeric matrix that contains a cross-linkable polymer.

It is a further aspect of the invention to provide such a method which involves the incorporation of air, carbon dioxide, oxygen, nitrogen, noble gases, or other gas or gases into a polymeric matrix such that the resulting therapeutic agent-containing polymeric reservoir has a relatively high surface area with respect to the amount of polymeric matrix used.

It is still a further aspect of the invention to provide a method for preparing a therapeutic agent-containing polymeric foam reservoir capable of transdermally delivering peptides, proteins, or fragments thereof.

It is still another aspect of the invention to provide an electrotransport drug delivery device capable of cost-effectively delivering peptides, proteins, or fragments thereof.

Additional aspects, advantages and novel features of the invention will be set forth in part in the description which follows, and in part will become apparent to those skilled in the art upon examination of the following, or may be learned by practice of the invention.

In one embodiment of the invention, then, a method is provided for making a therapeutic agent-containing polymeric reservoir having a predetermined volume for incorporation into an electrotransport agent delivery system adapted to deliver the therapeutic agent by electrotransport through an animal body surface. The method comprises placing a predetermined amount of the therapeutic agent in a polymer matrix to produce a drug-containing polymer matrix, foaming the polymer matrix with a gas, and cross linking the foamed matrix to produce a polymeric closed cell foam reservoir matrix having a predetermined pore volume. Once the foamed matrix is hydrated with a liquid solvent used to solubilize the therapeutic agent, the closed foam cells contain the gas and are substantially free of the therapeutic agent and the liquid solvent.

In a preferred embodiment of the invention, a method is provided for preparing a drug reservoir to be incorporated in an electrotransport drug delivery device, the method comprising foaming a polymeric mixture of polyvinyl alcohol by rapidly stirring the mixture in a selected atmosphere to produce a polymeric foam. A therapeutic agent is added to the polymeric foam, and the drug-containing foam is frozen and then allowed to warm to ambient temperature. Alternatively, the polymeric foam may be frozen and thawed, and a therapeutic agent added to the polymeric foam at a later time, but prior to its use in conjunction with the electrotransport drug delivery device.

In another embodiment of the invention, a therapeutic agent-containing polymeric reservoir having a predetermined volume is provided which comprises a chemically cross-linked polymeric closed-cell foam matrix containing a predetermined amount of the therapeutic agent and a predetermined volume percent of closed foam cells.

In still another embodiment of the invention, a therapeutic agent-containing polymeric reservoir having a predetermined volume is provided which comprises a polymeric closed-cell foam matrix cross-linked by exposure to actinic radiation and which contains a predetermined amount of the therapeutic agent and a predetermined volume percent of closed foam cells.

In a further embodiment of the invention, an electrotransport drug delivery system is provided which incorporates the aforementioned polymeric foam reservoir. The system contains a donor electrode, a counter electrode, a source of electrical power, and the polymeric reservoir containing the therapeutic agent to be delivered, typically present as part of the donor electrode.

MODES FOR CARRYING OUT THE INVENTION

Figure 1:
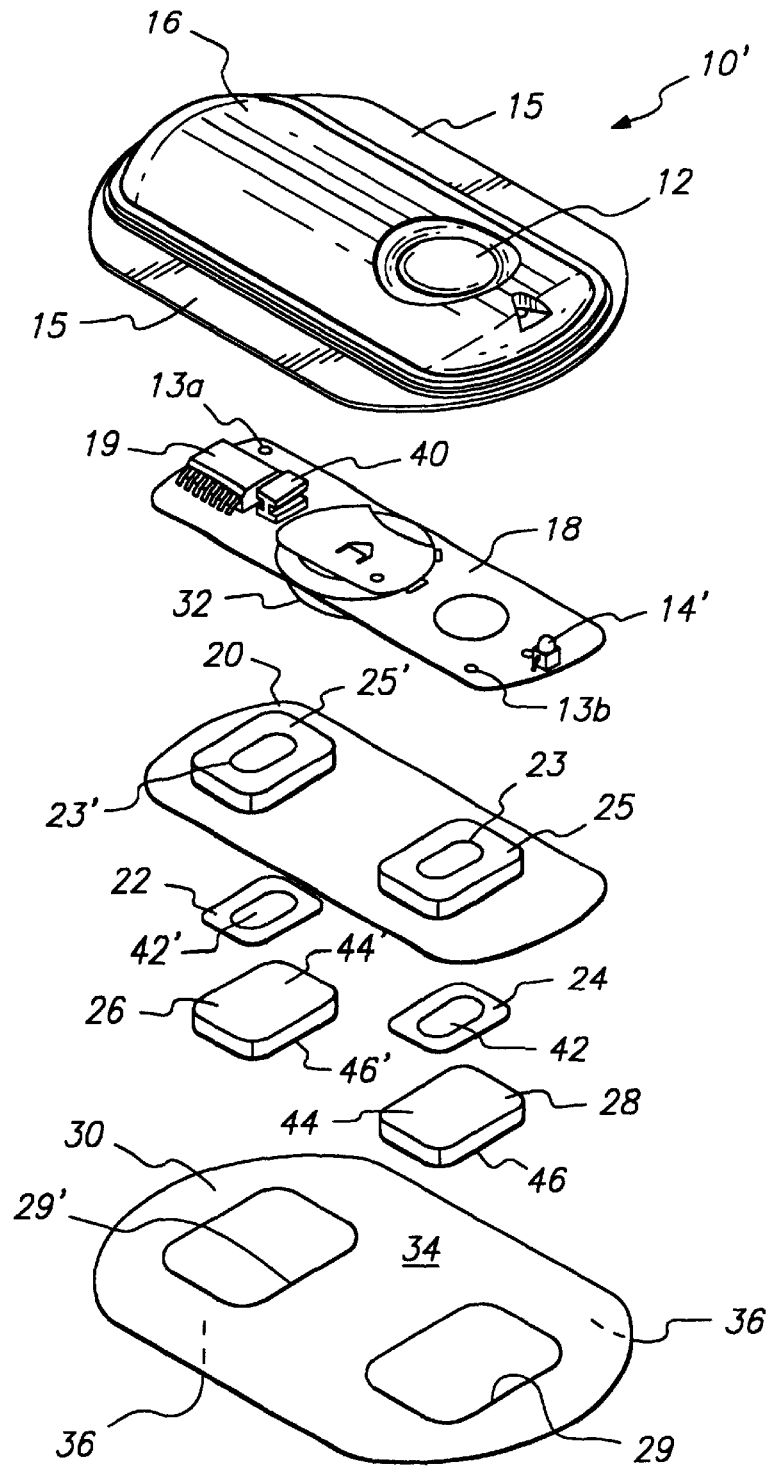
FIG. 1 is a perspective exploded view of one embodiment of an electrotransport drug delivery system which may be used in conjunction with drug formulations made using the inventive method.

Before describing the present invention in detail, it is to be understood that this invention is not limited to particular drugs, carriers, electrotransport delivery systems, or the like, as such may vary.

It must be noted that, as used in this specification and the appended claims, the singular forms "a", "an" and "the"

include plural referents unless the context clearly dictates otherwise. Thus, for example, reference to "a drug" or "a therapeutic agent" includes a mixture of two or more drugs or agents, reference to "a polymer" includes two or more polymers, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following specific terminology will be used in accordance with the definitions set out below.

By the terms "therapeutic agent," "drug" or "pharmaceutically active agent" as used herein is meant any chemical material or compound which induces a desired local or systemic therapeutic effect, and is capable of being delivered by electrotransport. Examples of such substances will be set forth below.

The term "solvent-containing polymer" refers to a polymer that can contain by absorption and/or adsorption an amount of any liquid solvent capable of dissolving a therapeutic agent of interest and/or the salt form of the agent in an amount sufficient to allow ions to pass while current is applied to a drug reservoir containing such polymer that is incorporated into an electrotransport drug delivery device. Preferably, the polymer will be capable of containing at least about 20 wt. % of the solvent. A particularly preferred solvent is water due, at least in part, to its excellent biocompatibility. A "hydrogel" is a solvent-containing polymer capable of absorbing at least about 20 wt. % of water.

By "polymer matrix" is intended to refer to a solution of a polymer in an appropriate solvent, a solvent-containing polymer that has swollen by absorption or adsorption of the solvent, a composition comprising a dispersed, solvent-containing polymer phase combined with a continuous, solvent phase to form a viscous, colloidal composition, or other form of polymer matrix that has the chemical and/or physical characteristics that allow the formation of a foamed polymeric matrix therefrom, e.g., viscosity, surfactant properties, and the like.

By "foaming a polymer matrix" is intended to mean a process whereby a plurality of gas-containing pockets or "cells" is introduced throughout a polymer matrix, thereby producing a "foamed polymer matrix." A "closed-cell polymer foam" is a foamed polymer matrix in which gas-containing cells are discrete and the gas phase of each cell is independent of that of the other cells.

The method of the invention involves foaming a therapeutic agent-containing polymeric matrix and cross linking the foamed matrix. The polymeric matrix is typically, although not necessarily, an aqueous solution, preferably containing between about 1 wt. % to 50 wt. % polymer. Relatively small quantities of the therapeutic agent, between about 0.001 wt. % to about 10 wt. %, preferably 0.01 wt. % to about 3 wt. %, and more preferably about 0.1 wt. % to about 2 wt. % of total admixture, is all that is typically required. Alternatively, the therapeutic agent may be incorporated into the foamed polymeric matrix after the foaming process is complete.

Suitable polymers that may be used to prepare a foamed polymeric matrix and cross linked to provide the foamed reservoir include polyvinyl alcohols, polyvinyl pyrrolidones, cellulosic polymers, e.g., hydroxyethyl cellulose, hydroxypropyl cellulose, hydroxypropyl methylcellulose, carboxymethyl cellulose, and the like, polyurethanes, polyethylene oxides, polyanhydrides, polyvinyl pyrrolidone/vinyl acetate copolymers, mixtures of these polymers and copolymers, and the like. One preferred polymer is polyvinyl alcohol.

Foaming a polymer matrix may be accomplished by any chemical or physical method known in the art. Typically, cellular polymers may be made by extrusion, spraying, frothing, compression molding, injection molding, sintering, leaching, or the like. Foam formation may be accomplished by stirring a polymer solution with a high speed, high shear mixing apparatus and/or by an apparatus that injects gas into a solution of the polymer. See Perkins et al. (1983) National Technical Conference, Am. Assoc. Textile Chemists and Colorists, pp. 147–151, for a schematic diagram of a foam generating device.

In one preferred method, foaming is accomplished by rapidly stirring a solution of the polymer in a selected atmosphere of air, carbon dioxide, oxygen, nitrogen, noble gases, other gas or gases, or mixtures thereof. The stirring causes gas from the selected atmosphere to be incorporated into the matrix, forming bubbles within the matrix. The gas bubbles act as an inert filler, increasing the surface area of the matrix without introducing the drawbacks of common "inert" fillers, such as glass beads, titanium dioxide, quartz powder, polymer powders, etc., to which therapeutically active agents may bind.

Another preferred method of preparing a foamed polymer matrix is by decompression expansion. In this method, a solution of a volatile blowing agent in molten polymer is formed in an extruder under pressure. The solution is forced through an orifice onto a receiving substrate at ambient temperature and pressure. The volatile blowing agent evaporates and causes the polymer to expand. Dimensional stability is achieved upon cooling or other cross-linking method as described below.

Yet another preferred method for foaming a polymeric matrix that is particularly preferred when the polymer matrix comprises polyvinyl alcohol, is by a frothing process because it can be performed at ambient temperature. The frothing process involves dispersing a gas in a fluid that has surface properties suitable for producing a foam. The foam can be permanently stabilized by cross-linking as described below.

Optionally, foam formation-enhancing additives can be added to the polymeric matrix prior to the foaming process. Examples of such additives include anionic surfactants, e.g., sodium lauryl sulfate, nonionic surfactants, e.g., ethyoxylated linear alcohols and ethoxylated alkyl phenols, and soaps, e.g., ammonium stearate.

A technical consideration in a foam system is that the foam must have a workable viscosity. High viscosity polymeric matrices are generally more difficult to foam and form foams having high viscosity. The viscosity of a foam prepared from a low viscosity polymeric matrix depends on the blow ratio.

The volume of the polymeric foamed matrix is also a function of blow ratio as well as the cell size of the foamed matrix. The blow ratio relates to the ratio of the volume of the final foam product to the volume of the polymeric matrix. Thus, a blow ratio of 1 indicates a doubling in volume (ratio=1:1), with the total volume of the cell being about 50 vol. % of the polymeric matrix, while a blow ratio of 7 represents an 8-fold increase in volume, with the total volume of the cells being 87.5% of the polymeric matrix.

Accordingly, polymeric matrices can be prepared in which the total cell volume, i.e., the volume occupied by the gas component of the polymeric foamed matrix, is in the range of about 25 vol. % to about 90 vol. %.

The drug-containing polymeric foam is then cross-linked to produce a therapeutic agent-containing closed-cell polymeric foam. Cross-linking may be accomplished by any method known in the art. In particular, cross-linking may be accomplished by freezing and thawing the matrix, by exposing the matrix to electromagnetic radiation or by incorporating a chemical cross-linking agent in the matrix.

Preferably, if the polymeric matrix is prepared from polyvinyl alcohol, the foamed polymeric matrix is cross-linked by freezing and thawing the matrix. The foamed polymeric matrix is frozen at a temperature in the range of $-10°$ C. to $-35°$ C., typically around $-20°$ C., for hold-time of at least about 15 seconds to about 24 hours, preferably about 30 seconds to 12 hours, more preferably about 30 seconds to 2 hours. The foam is then allowed to warm to a thaw temperature in the range of about $-5°$ C. to about 20° C., i.e., ambient temperature, preferably $-5°$ C. to about 5° C., more preferably $-5°$ C. to 0° C., at which point it may be incorporated directly into an electrotransport drug delivery system. The dwell-time at the thaw temperature ranges can be as long as 24 hours, preferably in the range of about 1 to 12 hours, more preferably about 1 hour to six hours. In general, the extent of cross-linking increases in direct proportion with the thaw temperature and the dwell-time at that temperature. Optionally, the freeze/thaw cycle may be repeated at least once and as many as 10 or more times. Preferably, the freeze/thaw cycle is repeated between about 1 and 5 times. This freeze/thaw cycle allows the polymeric matrix to form physical cross-links without the need for chemical cross-linking agents such as formaldehyde, glyoxal and butyraldehyde, which are known skin irritants and may be difficult to remove from the foamed polymer matrix. Additional cycles of freezing and thawing typically yields a foam with greater density and structural rigidity. The preparation of polyvinyl alcohol matrices by freeze/thaw cycling has been described in, e.g., U.S. Pat. Nos. 4,524,064, 4,664,857 and 4,925,603 to Nambu, U.S. Pat. No. 4,734,097 to Tanabe et al., U.S. Pat. No. 4,808,353 to Nambu et al., U.S. Pat. No. 4,988,771 to Ikada et al., and U.S. Pat. No. 5,141,973 to Kobayashi et al.

Alternatively, the foamed polymeric matrix may be cross-linked by exposure to electromagnetic radiation, such as electron beam radiation, gamma radiation, ultraviolet radiation, and the like. Typically, a polymer solution is prepared and foamed as described above and then exposed to electromagnetic radiation by methods well known in the art to cross-link the polymer and trap the gas bubbles in a closed cell structure. Since many drugs may be degraded by exposure to most forms of electromagnetic radiation, it is preferred that the therapeutic agent is added to the polymeric matrix after the cross linking process is complete. The therapeutic agent may be incorporated into the cross-linked polymeric matrix by impregnation, absorption or the like.

An additional means for cross-linking the foamed polymeric matrix is by incorporating a chemical cross-linking agent into the matrix. Examples of cross-linking agents include aldehydes, epoxides, borax, diisocyanates, and the like, and mixtures thereof; the specific cross-linking agent will depend on the polymer used to prepare the foamed polymeric matrix. For example, cellulosic polymers can be cross-linked using formaldehyde or various N-methylol compounds, e.g., hydantoins, triazones, and the like, in the presence of a strong acid, diepoxides, e.g., vinylcyclohexene dioxide, butadiene dioxide, diglycidyl ether, and the like, in the presence of strong bases, and aziridine compounds, e.g., tris(1-aziridinyl)phosphine oxide and tris(aziridinyl) triazine. Polyurethanes may be cross-linked using aromatic isocyanates such as toluene diisocyanate and 4,4'diphenylmethane diisocyanate and aliphatic isocyanates such as isophorone diisocyanate, hydrogenated 4,4'-diphenylmethane diisocyanate, trimerized hexamethylene diisocyanate. A sufficient amount of cross-linking agent is used to produce the desired extent of cross-linking and density of the foamed polymerix matrix, but preferably less than that which would result in any unconsumed material. However, if excess cross-linking agent is present after foamed polymeric matrix formation, it is preferably removed using a simple washing step.

The method of the invention alternatively may involve foaming a polymeric mixture, without the therapeutic agent to be delivered. For example, rapid stirring of the mixture (which is typically, again, an aqueous solution) in a selected atmosphere of air, carbon dioxide, oxygen, nitrogen, noble gases, other gas or gases, or mixtures thereof may be used to produce a polymeric foam. Then, the therapeutic agent is added to the polymeric foam by impregnation, absorption, or the like, and the therapeutic agent-containing foam is cross-linked as described above to produce a cross-linked polymeric matrix.

Alternatively, the therapeutic agent may be incorporated into the cross-linked polymeric matrix, again, by impregnation, absorption or the like. The resulting therapeutic agent-containing matrix may then be used as a drug reservoir in an electrotransport drug delivery system.

As noted above, drugs, therapeutic or active agents useful in connection with the present invention include any pharmaceutical compound or chemical that is capable of being delivered by electrotransport. In general, this includes agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetrics, prostaglandins, psychostimulants, sedatives and tranquilizers. The invention is particularly useful in conjunction with the electrotransport delivery of proteins, peptides and fragments thereof, whether naturally occurring, chemically synthesized or recombinantly produced.

With respect to the delivery of peptides, polypeptides, proteins and other such species, these substances typically have a molecular weight of at least about 300 daltons, and more typically have a molecular weight of at least about 300 to 40,000 daltons. Specific examples of peptides and proteins in this size range include, without limitation, GHRH, GHRF, insulin, insultropin, calcitonin, octreotide, endorphin, TRH, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc.), follicle luteoids, αANF, growth factors such as growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, CD4, ceredase, CSI's, enkephalins, FAB fragments, IgE peptide suppressors, IGF1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

Luteinizing hormone-releasing hormone ("LHRH") and LHRH analogs such as goserelin, buserelin, gonadorelin, napharelin and leuprolide, represent another class of peptides and proteins in this size range that are useful in connection with the present invention. One preferred LHRH analog is goserelin. Goserelin is a synthetic decapeptide analogue of LHRH having the chemical structure pyro-Glu-His-Trp-Ser-Tyr-D-Ser(But)-Leu-Arg-Pro-Azgly-$NH_2$. The drug is useful in the treatment of prostate and breast cancers and in certain gynecological conditions.

It will be appreciated by those working in the field that the present method can be used in conjunction with a wide variety of electrotransport drug delivery systems, as the method is not limited in any way in this regard. For examples of electrotransport drug delivery systems, reference may be had to U.S. Pat. Nos. 5,147,296 to Theeuwes et al., 5,080,646 to Theeuwes et al., 5,169,382 to Theeuwes et al., and 5,169,383 to Gyory et al., the disclosures of which are incorporated by reference herein.

FIG. 1 illustrates a representative electrotransport delivery device that may be used in conjunction with the present drug reservoirs. Device 10 comprises an upper housing 16, a circuit board assembly 18, a lower housing 20, anode electrode 22, cathode electrode 24, anode reservoir 26, cathode reservoir 28, and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

Device 10 is generally comprised of battery 32, electronic circuitry 19,40, electrodes 22,24, and polymeric foam matrix drug reservoirs 26,28, all of which are integrated into a self-contained unit. The outputs (not shown in FIG. 1) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrode/reservoirs 22,26 and 24,28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of light-emitting diode ("LED") 14 becoming lit and/or an audible sound signal from, e.g., a "beeper". Drug is delivered through the patient's skin by electrotransport, e.g., on the arm, over the predetermined delivery interval.

Anodic electrode 22 is preferably comprised of silver and cathodic electrode 24 is preferably comprised of silver chloride. Both reservoirs 26 and 28 are comprised of foamed polymeric materials as described above. Electrodes 22,24 and reservoirs 26,28 are retained by lower housing 20.

The polymeric foam matrix reservoirs 26 and 28 contain drug solution uniformly dispersed in at least one of reservoirs 26 and 28. Drug concentrations in the range of approximately $1\times10^{-6}$ M to 1.0 M or more can be used, with drug concentrations in the lower portion of the range being preferred.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and polymeric foam matrix drug reservoirs within housing depression 25,25' as well as retains lower housing 20 attached to upper housing 16.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Preparation of 10 wt. % Polyvinyl Alcohol Polymeric Foam Reservoir

A commercial grade of polyvinyl alcohol (average degree of polymerization=5100; average molecular weight=224 kDa; degree of hydrolysis=99.7 mol. %) was purified by extraction with three portions deionized water and one portion isopropyl alcohol. A 10 wt. % solution of polyvinyl alcohol was prepared by heating a mixture of 10.0 gm of the purified polyvinyl alcohol in 90.0 gm of deionized water at 90° C. for approximately 70 minutes. The polyvinyl alcohol solution was allowed to cool to ambient temperature and a 20.0 gm aliquot of the solution was transferred into a beaker. The solution was stirred vigorously with a pitched turbine blade (Caframo mixer) at a rate of about 2000 rpm. Approximately 50 mL of a white foam was obtained after about one hour of stirring.

The foam was poured into cylindrical ethylene vinyl acetate molds having a dimension of 8 $cm^2$ by 0.16 cm, and frozen in an environmental chamber at about −20° C. for about 24 hours. The frozen foam was then removed from the environmental chamber and allowed to warm to ambient temperature. The resulting cross-linked polymer matrix was soft and spongy, and maintained acceptable structural integrity for at least two weeks at ambient temperature.

EXAMPLE 2

Preparation of a 10 wt. % Polyvinyl Alcohol Polymeric Foam Reservoir Cross-linked Using Freeze-Thaw Cycling A polyvinyl alcohol foam prepared and poured into a mold as described in Example 1 was cross-linked by exposure to 3 cycles of freezing at −20° C. for 2 hours and warming to 5° C. for 30 minutes. The polyvinyl alcohol foam was cross-linked and had a greater cross-link density than with a single 24-hour exposure at −20° C. as described in Example 1 and resulted in a more structurally rigid foam.

EXAMPLE 3

Preparation of Citrate-buffered 15 wt. % Polyvinyl Alcohol Polymeric Foam Reservoir The methods described in Examples 1 and 2 are used to make polymeric foam reservoirs using a solution containing 15 wt. % polyvinyl alcohol, 0.24 wt. % citric acid, 0.37 wt. % trisodium citrate and 0.1 wt. % sodium chloride instead of a 10 wt. % solution of polyvinyl alcohol.

EXAMPLE 4

Preparation of 15 wt. % Polyvinyl Alcohol Polymeric Foam Reservoir Containing Goserelin Acetate The methods described in Examples 1 and 2 are used to make polymeric foam reservoirs using a solution containing 15 wt. % polyvinyl alcohol and 1.5 mM goserelin instead of a 10 wt. % solution of polyvinyl alcohol.

EXAMPLE 5

Preparation of 15 wt. % Polyvinyl Alcohol Polymeric Foam Reservoir Containing Fentanyl Hydrochloride The methods described in Examples 1 and 2 are used to make polymeric foam reservoirs using a solution containing 15 wt. % polyvinyl alcohol, 1.74 wt. % fentanyl hydrochloride and 0.17 wt. % urocanic acid instead of a 10 wt. % solution of polyvinyl alcohol.

EXAMPLE 6

Electrotransport Studies Using a Polymeric Foam Reservoir Containing Goserelin

Permeation Cell Assembly

Electrotransport studies can be conducted using two-compartment polycarbonate permeation cells designed to evenly support drug-containing foamed polymeric matrices. A silver chloride extruded laminate is overlaid on an electrode support and sealed to the receptor compartment using double-sided adhesive tape. Human cadaver epidermis (abdomen, 2 $cm^2$) is adhered to the grid support on the receptor cell using adhesive tape, with the stratum corneum facing the donor compartment.

The drug-containing polymeric foam reservoir containing goserelin prepared as described in Example 4 is seated into the anode housings consisting of a silver electrode and a foam mold. This assembled donor compartment is overlaid onto the epidermis and the electrode support is secured to complete the permeation cell.

Preparation of Human Epidermis

Heat-stripped human epidermis is used for the electrotransport studies. The epidermis is separated from the dermal layer by immersing the tissue in water at 60° C. for 90 seconds.

Preparation of Solutions

The receptor solution consists of full strength, 0.15 M Dulbecco's phosphate buffered saline ("DPBS"), pH 7.4.

Analytical Methods

In vitro delivery samples are analyzed as follows: a 1 mL sample is transferred to a polypropylene scintillation vial and 10 mL Ready Safe® scintillation cocktail was added to the vial. The vial is shaken gently and placed in the liquid scintillation counter.

EXAMPLE 7

Electrotransport Studies Using a Polymeric Foam Reservoir Containing Fentanyl Hydrochloride The methods of Example 6 substituting the polymeric foam reservoir containing fentanyl hydrochloride as described in Example 5 are used to study the electrotransport delivery of fentanyl hydrochloride.

What is claimed is:

1. A method of making a therapeutic agent-containing polymeric reservoir having a predetermined volume, the reservoir to be incorporated into an electrotransport agent delivery system adapted to deliver the therapeutic agent by electrotransport through an animal body surface, comprising the steps of:

(a) providing a polymer matrix;

(b) performing a step selected from the group consisting of:

i. placing a predetermined amount of the therapeutic agent in the polymer matrix and then foaming the polymer matrix with a gas to produce a polymeric foam matrix:
   ii. simultaneously adding a predetermined amount of the therapeutic agent to the polymer matrix while foaming the polymer matrix with a gas to produce a polymeric foam matrix; and
   iii. foaming the polymeric matrix with a gas to produce a polymeric foam matrix and then adding a predetermined amount of the therapeutic agent to the polymeric foam matrix;

(c) cross-linking the polymeric foam matrix to produce a polymeric closed-cell foam matrix reservoir having a predetermined pore volume, the matrix, upon hydration with a liquid solvent used to solubilize the therapeutic agent, having closed foam cells containing the gas and said closed foam cells being substantially free of the therapeutic agent and the liquid solvent and wherein the closed foam cells comprise about 25 to about 90 vol % of the polymeric foam matrix.

2. The method of claim 1, wherein the polymeric foam matrix is cross-linked using electromagnetic radiation, a chemical cross-linking agent or a freeze/thaw cycle.

3. The method of claim 2, wherein the polymer is selected from the group consisting of polyvinyl alcohols, polyvinyl pyrrolidones, cellulosic polymers, polyurethanes, polyethylene oxides, polyanhydrides, polyvinyl pyrrolidone/vinyl acetate copolymers, and mixtures thereof.

4. The method of claim 2, wherein the cross-linking is accomplished by means of a chemical cross-linking agent.

5. The method of claim 4, wherein the chemical cross-linking agent is selected from the group consisting of aldehydes, epoxides, borax, diisocyanates, and mixtures thereof.

6. The method of claim 1, wherein the cross linking of the foamed matrix is accomplished by freezing and thawing the matrix.

7. The method of claim 6, wherein the polymer comprises polyvinyl alcohol.

8. The method of claim 1, wherein the therapeutic agent is a protein, a polypeptide, or a fragment thereof.

9. The method of claim 1, wherein the gas is selected from the group consisting of air, carbon dioxide, oxygen, nitrogen, noble gases, and mixtures thereof.

10. A therapeutic agent-containing polymeric reservoir for an electrotransport therapeutic agent delivery system, the reservoir having a predetermined volume, the reservoir comprising a cross-linked polymeric closed-cell aqueous foam matrix containing a predetermined amount of the therapeutic agent and a predetermined volume percent of closed foam cells, the matrix, upon hydration with a liquid solvent used to solubilize the therapeutic agent, having closed foam cells containing a gas and being substantially free of the therapeutic agent and the liquid solvent wherein said closed foam cells comprise about 25 to about 90 vol % of the polymeric matrix.

11. The reservoir of claim 10, wherein the polymer matrix is electromagnetic radiation cross-linked, chemically cross-linked or freeze/thaw cross-linked.

12. The reservoir of claim 10, wherein the polymer is an electron beam cross-linked polymer selected from the group consisting of polyvinyl alcohols, polyvinyl pyrrolidones, cellulosic polymers, polyurethanes, polyethylene oxides, polyanhydrides, polyvinyl pyrrolidone/vinyl acetate copolymers, and mixtures thereof.

13. The reservoir of claim 10, wherein the polymer is a chemically cross-linked polymer selected from the group consisting of polyvinyl alcohols, polyvinyl pyrrolidones, cellulosic polymers, polyurethanes, polyethylene oxides, polyanhydrides, polyvinyl pyrrolidone/vinyl acetate copolymers, and mixtures thereof.

14. The reservoir of claim 10, wherein the polymer comprises a freeze/thaw cross-linked polyvinyl alcohol.

15. The reservoir of claim 10, wherein the therapeutic agent is a drug.

16. The reservoir of claim 10, wherein the therapeutic agent is a protein, a polypeptide, or a fragment thereof.

17. The reservoir of claim 10, wherein the gas is selected from the group consisting of air, carbon dioxide, oxygen, nitrogen, noble gases, and mixtures thereof.

18. An electrotransport delivery device comprising the reservoir of claim 10.

19. An electrotransport device for delivering a therapeutic agent through an animal body surface, the device comprising a donor electrode, a counter electrode, and a source of electrical power adapted to be electrically connected to the donor electrode and the counter electrode, the donor electrode being electrically connected to the therapeutic agent-containing reservoir of claim 10.

* * * * *

UNITED STATES PATENT AND TRADEMARK OFFICE
CERTIFICATE OF CORRECTION

PATENT NO. : 6,650,934 B2 Page 1 of 1
APPLICATION NO. : 08/966437
DATED : November 18, 2003
INVENTOR(S) : Thomas O. Murdock It is certified that error appears in the above-identified patent and that said Letters Patent is hereby corrected as shown below:

On the title page, please insert the missing item "(73) Assignee" which should read as the follows:

-- (73) Assignee: ALZA Corporation, Mountain View, CA --

Signed and Sealed this

Sixth Day of March, 2007

JON W. DUDAS
*Director of the United States Patent and Trademark Office*